United States Patent [19]

Diveley

[11] 4,259,260

[45] Mar. 31, 1981

[54] SOLVENT PROCESS FOR HYDROLYZING 5-ISOTHIOCYANO-5,6-DIHYDRODICYCLOPENTADIENE

[75] Inventor: William R. Diveley, Wilmington, Del.

[73] Assignee: Boots Hercules Agrochemicals Co., Wilmington, Del.

[21] Appl. No.: 114,441

[22] Filed: Jan. 22, 1980

[51] Int. Cl.³ ............................................. C07C 83/00
[52] U.S. Cl. ................................................... 564/459
[58] Field of Search ..................................... 260/563 P

[56] References Cited

U.S. PATENT DOCUMENTS

| | | | |
|---|---|---|---|
| 3,088,977 | 5/1963 | Segel | 260/563 P |
| 3,150,183 | 9/1964 | Buntin | 260/563 P |
| 3,154,579 | 10/1964 | Flanagan | 260/563 P |
| 3,238,251 | 3/1966 | Williams | 260/563 P X |
| 3,304,167 | 2/1967 | Buntin et al. | 260/563 P X |

OTHER PUBLICATIONS

"J. Org. Chem.", 34, pp. 616–624, 1969.

*Primary Examiner*—Paul F. Shaver
*Attorney, Agent, or Firm*—Richard J. Sheridan; George H. Hopkins

[57] ABSTRACT

5-Isothiocyano-5,6-dihydro-dicyclopentadiene is hydrolyzed with caustic to 5-amino-5,6-dihydro-dicyclopentadiene in a reaction medium comprising a polar organic liquid which is inert under the reaction conditions and which at least partially dissolves the reactants and products.

4 Claims, No Drawings

SOLVENT PROCESS FOR HYDROLYZING 5-ISOTHIOCYANO-5,6-DIHYDRODICYCLOPENTADIENE

This invention relates to the conversion of 5-isothiocyano-5,6-dihydro-dicyclopentadiene having the formula:

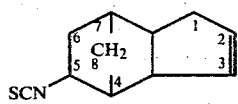
(I)

to 5-amino-5,6-dihydro-dicyclopentadiene having the formula:

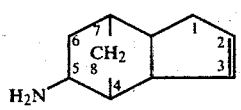
(II)

Methods for converting an organic isothiocyanate to an organic amine are disclosed in the prior art. U.S. Pat. No. 3,150,183 to Buntin discloses such a conversion by reacting the organic isothiocyanate with elementary chlorine and water in either a one- or two-step process. While Buntin does convert from isothiocyanate to amine, his process is not applicable to the present invention. Buntin's conversion process involves isothiocyanates containing an alicyclic organic radical which is a saturated hydrocarbon or chlorohydrocarbon radical. The isothiocyanates of this invention contain an unsaturated organic radical. Thus, the use of elementary chlorine for the conversion of the isothiocyanates of this invention would lead to the undesirable loss of the unsaturation in the organic radical via attack by the chlorine.

U.S. Pat. No. 3,304,167 to Buntin and Diveley further discloses a two-step hydrolysis process for converting an isothiocyanate to an amine by first reacting the isothiocyanate with ammonia to form a thiourea and then treating the thiourea with NaOH to produce an amine.

As disclosed by Buntin and Diveley in U.S. Pat. No. 3,304,167, the hydrolysis of an isothiocyanate by caustic or related base to an amine involves the formation of a thiourea intermediate which, in the present invention, is 1,3-bis[5-(5,6-dihydro-dicyclopentadienyl)]-2-thiourea having the formula:

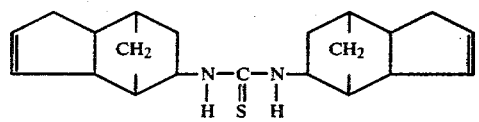
(III)

As the amine is formed during the hydrolysis of the isothiocyanate, it reacts rapidly with the unreacted isothiocyanate present in the reaction mixture to form the thiourea. Due to the high insolubility of the thiourea in the aqueous reaction mixture, the reaction stops. The thiourea must then be recovered and converted to the amine. Buntin and Diveley accomplish this by using ethylene glycol as the solvent for the hydrolysis of the thiourea to the amine. This process has a serious drawback, however, in that there is no satisfactory way known to recover and recycle the ethylene glycol economically due to its solubility in water.

The present invention obviates the necessity of such an involved multi-step process by providing a hydrolysis process for the conversion of 5-isothiocyano-5,6-dihydro-dicyclopentadiene to 5-amino-5,6-dihydro-dicyclopentadiene which allows the conversion to take place in a single-step process. This single-step comprises hydrolyzing the isothiocyanate with caustic in a reaction medium in which he caustic, isothiocyanate, thiourea intermediate, and amine are at least partially soluble. More particularly, the process of this invention involves the conversion of 5-isothiocyano-5,6-dihydro-dicyyclopentadiene to 5-amino-5,6-dihydro-dicyclopentadiene by reacting the isothiocyanate and caustic in a reaction medium comprising a polar organic liquid which is inert under the reaction conditions and which at least partially dissolves the reactants and products, including the intermediate thiourea. Examples of organic liquids which are useful in the practice of this invention include alcohols containing three or more carbon atoms. By carrying out the reaction in such an alcohol, the thiourea intermediate which forms does not separate from the reaction mixture, as is the case with caustic hydrolysis in an aqueous medium at atmospheric pressure, and the conversion to a amine continues to completion.

The term caustic as used herein refers to strongly alkaline materials, such as, for example, alkali metal hydroxides, or aqueous solutions thereof. Preferred caustics are NaOH and KOH.

The conversion of the isothiocyanate to the amine is illustrated by the following equation wherein R represents the dicyclopentadiene radical:

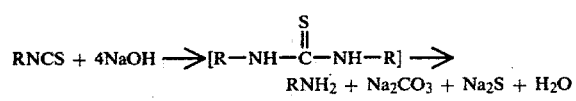

Thus, it can be seen that a molar ratio of NaOH to isothiocyanate of at least 4 to 1 is required for the conversion to be complete. Preferably, excess NaOH is used such as, for example, a 5 to 1 molar ratio, to assure complete conversion.

There are several criteria used for the selection of the organic liquids useful as the reaction medium in the process of this invention. First, the organic liquid must be capable of at least partially dissolving the reactants (i.e., the isothiocyanate and the caustic), the thiourea intermediate, and the product sufficiently for the hydrolysis to proceed to completion. Second, a temperature of at least about 80° C. is required to initiate and sustain the reaction at practical rates. While the reaction can be run under superatmospheric conditions which would allow organic liquids with atmospheric boiling points below about 80° C. to be heated above that temperature, it is preferable to run the reaction at atmospheric pressure. Therefore, the organic liquid should have an atmospheric pressure boiling of at least about 80° C. in order that the reaction mixture can be heated to the required temperature to initiate and sustain the reaction at practical rates. Most preferably, the organic liquid should have an atmospheric boiling point such that the reaction mixture will reflux at about 120°–160° C. thereby automatically controlling the temperature of the reaction mixture. However, higher boiling organic liquids may be used if temperature control means, e.g., a thermostat, is employed. Third, it is preferred that the organic liquid be relatively water-insoluble to facilitate both recovery of the product and recycle of the organic liquid since water is preferably added to the reaction mixture during recovery of the product to remove the inorganic salt by-products. Finally, the organic liquid should be relatively economical, i.e., both inexpensive and recoverable for recycle.

It has been found that the above criteria are satisfied by alcohols containing three or more carbon atoms. A preferred group of such alcohols includes the $C_4$–$C_{16}$ alcohols, especially 1-butanol, 1-pentanol and 1-hexanol. A particularly preferred alcohol is 1-hexanol since its higher boiling point allows higher reaction temperatures to be achieved, thereby providing faster reaction rates and correspondingly shorter reaction times. Other organic liquids besides alcohols may be used in the process of this invention if they meet the criteria given above.

The amines produced by the process of this invention are useful as chemical intermediates for the synthesis of herbicidally active compounds such as those disclosed in U.S. Pat. No. 3,304,167 to Buntin and Diveley.

The following examples illustrate the process of this invention. Unless otherwise indicated all parts and percentages in the examples and throughout this specification are by weight.

EXAMPLE 1

A suitable vessel is charged with 81.6 g. (2.0 moles) of NaOH and 250 ml. of 1-hexanol. The resulting mixture is stirred and heated to refluxing temperature. To this refluxing mixture is added 76.4 g. of 5-isothiocyano-5,6-dihydro-dicyclopentadiene (0.364 mole based on 91% purity of the isothiocyanate) dropwise over about 2 hours. During this time the refluxing temperature drops from about 166° C. to about 150° C. and come solids separate. Refluxing is continued for 4 hours after all of the isothiocyanate is added. The resulting mixture is cooled to about 95° C. and 250 ml. of water is added. Almost all of the solids dissolve.

The resulting mixture is suction filtered and the filtrate transferred to a separatory funnel using 25 ml. of 1-hexanol wash. The mixture separates into aqueous and organic layers.

The organic layer is separated from the aqueous layer and washed with 100 g. of 20% NaCl. Again organic and aqeuous layers separate. The organic layer is recovered as a dark tan liquid (typical quantity is 248.0 g.).

Analysis of this organic layer shows it contains the product 5-amino-5,6-dihydro-dicyclopentadiene (typical amount is 22.05% of the organic layer which corresponds to an essentially quantitative yield of the product amine).

The organic layer may be fractionally distilled to recover the 1-hexanol for recycle and isolate the product, 5-amino-5,6-dihydro-dicyclopentadiene.

EXAMPLE 2

76.4 g. of 5-isothiocyano-5,6-dihydro-dicyclopentadiene is added dropwise over 2 hours at refluxing temperature to a stirred mixture of 485 ml. of 1-butanol, 15 ml. of water and 96.0 g. of NaOH. The resulting reaction mixture is maintained at refluxing temperature of about 120° C. for 12 hours.

The product, 5-amino-5,6-dihydro-dicyclopentadiene, is recovered, following the procedure of Example 1, in essentially quantitative yield.

EXLAMPLE 3

The procedure described in Example 1 is repeated using 80.0 g. of NaOH, 76.4 g. of 5-isothiocyano-5,6-dihydro-dicyclopentadiene and, instead of the 1-hexanol used in Example 1, 500 ml. of 1-pentanol. The isothiocyanate is added over about 2-¼ hours at a refluxing temperature of about 120° C. is maintained for 8 hours thereafter.

The product, 5-amino-5,6-dihydro-dicyclopentadiene, is recovered, following the procedure of Example 1, in essentially quantitative yield.

Other features, advantages and specific embodiments of this invention will become readily apparent to those exercising ordinary skill in the art after reading the foregoing disclosures. These specific embodiments are within the scope of the claimed subject matter unless otherwise expressly indicated to the contrary. Moreover, while a few specific embodiments of this invention have been described in considerable detail, variations and modifications of these embodiments can be effected without departing from the spirit and scope of the invention as disclosed and claimed.

What I claim and desire to protect by Letters Patent is:

1. A process of preparing 5-amino-5,6-dihydro-dicyclopentadiene, which comprises reacting 5-isothiocyano-5,6-dihydro-dicyclopentadiene and caustic in a reaction medium comprising a polar organic liquid which is inert under the reaction conditions and which at least partially dissolves the reactants and products.

2. The process of claim 1 wherein the polar organic liquid is an alcohol containing three or more carbon atoms.

3. The process of claim 2 wherein the alcohol is a $C_4$–$C_{16}$ alcohol.

4. The process of claim 3 wherein the $C_4$–$C_{16}$ alcohol is 1-hexanol.

* * * * *